US00PP23485P2

(12) United States Plant Patent
Beekenkamp

(10) Patent No.: US PP23,485 P2
(45) Date of Patent: Mar. 19, 2013

(54) ***DAHLIA* PLANT NAMED 'BKDAPDP'**

(50) Latin Name: *Dahlia hybrida*
Varietal Denomination: Bkdapdp

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 13/200,526

(22) Filed: Sep. 23, 2011

(51) Int. Cl.
*A01H 5/00* (2006.01)

(52) U.S. Cl. ..... Plt./321

(58) Field of Classification Search ..... Plt./321
See application file for complete search history.

*Primary Examiner* — Annette Para
(74) *Attorney, Agent, or Firm* — C. A. Whealy

(57) ABSTRACT

A new and distinct cultivar of *Dahlia* plant named 'Bkdapdp', characterized by its compact, upright and mounding plant habit; freely basal branching; dense and bushy growth habit; dark green-colored leaves; early and freely flowering habit; double inflorescences with dark pink-colored ray florets; and good garden performance.

2 Drawing Sheets

Botanical designation: *Dahlia hybrida.*
Cultivar denomination: 'BKDAPDP'.

BACKGROUND OF THE INVENTION

The present invention relates to a new and distinct cultivar of *Dahlia* plant, botanically known as *Dahlia hybrida* and hereinafter referred to by the name 'Bkdapdp'.

The new *Dahlia* plant is a product of a planned breeding program conducted by the Inventor in Maasdijk, The Netherlands. The objective of the breeding program is to create new container *Dahlia* plants that have a freely branching habit, attractive ray floret coloration, long flowering period and good garden performance.

The new *Dahlia* plant originated from an open-pollination in June, 2008 in Maasdijk, The Netherlands of a proprietary selection of *Dahlia hybrida* identified as code number 4001198, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled environment in Maasdijk, The Netherlands in August, 2009.

Asexual reproduction of the new *Dahlia* plant by cuttings in a controlled environment in Maasdijk, The Netherlands since November, 2009 has shown that the unique features of this new *Dahlia* plant are stable and reproduced true to type in successive generations.

SUMMARY OF THE INVENTION

Plants of the new *Dahlia* have not been observed under all possible environmental conditions and cultural conditions. The phenotype may vary somewhat with variations in environmental conditions such as temperature and light intensity, without, however, any variance in genotype.

The following traits have been repeatedly observed and are determined to be the unique characteristics of 'Bkdapdp'. These characteristics in combination distinguish 'Bkdapdp' as a new and distinct *Dahlia* plant:

1. Compact, upright and mounding plant habit.
2. Freely basal branching; dense and bushy growth habit.

3. Dark green-colored leaves.
4. Early and freely flowering habit.
5. Double inflorescences with dark pink-colored ray florets.
6. Good garden performance.

Compared to plants of the female parent selection, plants of the new *Dahlia* differ primarily in the following characteristics:

1. Plants of the new *Dahlia* are smaller than plants of the female parent selection.
2. Plants of the new *Dahlia* have smaller flowers than plants of the female parent selection.
3. Plants of the new *Dahlia* and the female parent selection differ in ray floret color as plants of the female parent selection have white-colored ray florets.

Plants of the new *Dahlia* can be compared to plants of *Dahlia* 'Micronetta Purple Pink', not patented. In side-by-side comparisons conducted in Maasdijk, The Netherlands, plants of the new *Dahlia* differed from plants of 'Micronetta Purple Pink' in the following characteristics:

1. Plants of the new *Dahlia* were more freely branching than plants of 'Micronetta Purple Pink'.
2. Plants of the new *Dahlia* had shorter peduncles than plants of 'Micronetta Purple Pink'.
3. Plants of the new *Dahlia* and 'Micronetta Purple Pink' differed slightly in ray floret color.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Bkdapdp' grown in a container.

The photograph on the second sheet is a close-up view of typical inflorescences and leaves of 'Bkdapdp'.

DETAILED BOTANICAL DESCRIPTION

The aforementioned photographs and the following observations and measurements describe plants grown during the summer in 12-cm containers in a glass-covered greenhouse in Maasdijk, The Netherlands and under environmental conditions and cultural practices which approximate those generally used in commercial container *Dahlia* production. During the production of the plants, day temperatures ranged from 17° C. to 19° C. and night temperatures ranged from 15° C. to 17° C. Plants were pinched one time and were 65 days old when the photographs and description were taken. In the following description, color references are made to The Royal Horticultural Society Colour Chart, 2007 Edition, except where general terms of ordinary dictionary significance are used.

Botanical classification: *Dahlia hybrida* 'Bkdapdp'.

Parentage:

*Female, or seed, parent*.—Proprietary selection of *Dahlia hybrida* identified as code number 4001198, not patented.

*Male, or pollen, parent*.—Unknown selection of *Dahlia hybrida*, not patented.

Propagation:

*Type*.—By cuttings.

*Time to initiate roots, summer*.—About 16 days at temperatures of about 18° C. to 21° C.

*Time to initiate roots, winter*.—About 19 days at temperatures of about 18° C. to 21° C.

*Time to produce a rooted young plant, summer*.—About 21 days at temperatures of about 18° C. to 21° C.

*Time to produce a rooted young plant, winter*.—About 23 days at temperatures of about 18° C. to 21° C.

*Root description*.—Medium in thickness, fibrous, white in color; tuber development has not been observed.

*Rooting habit*.—Moderate branching; medium density.

Plant description:

*Plant form and growth habit*.—Compact, upright and mounding plant form; shape roughly globular; four primary lateral branches develop, each primary lateral branch with numerous secondary branches; inflorescences held above the foliar plane on strong peduncles; bushy and dense growth habit.

*Plant height*.—About 16.4 cm.

*Plant diameter or spread*.—About 21.3 cm.

*Lateral branches*.—Length: About 7.6 cm. Diameter: About 6 mm. Internode length: About 9 mm. Aspect: About 30° from vertical. Strength: Strong. Texture: Smooth, glabrous. Color: Between 183A and N186C.

Foliage description:

*Arrangement*.—Leaves opposite; single.

*Length*.—About 7.3 cm.

*Width*.—About 4.7 cm.

*Shape*.—Broadly ovate.

*Apex*.—Acute.

*Base*.—Attenuate.

*Margin*.—Dentate to coarsely dentate.

*Venation pattern*.—Pinnate.

*Texture, upper surface*.—Sparsely pubescent.

*Texture, lower surface*.—Smooth, glabrous.

*Color*.—Developing leaves, upper surface: Close to N137A. Developing leaves, lower surface: Close to 138B. Fully expanded leaves, upper surface: Between N137A and 147A; venation, close to 152A strongly tinged with close to 177A. Fully expanded leaves, lower surface: Close to 194A to 194B; venation, close to 148A.

*Petioles*.—Length: About 2.8 cm. Diameter: About 4 mm. Texture, upper and lower surfaces: Smooth, glabrous. Color, upper surface: Close to 177A to 177B. Color, lower surface: Close to 146D.

Inflorescence description:

*Appearance and arrangement*.—Double inflorescence form with ray and disc florets forming acropetally on a receptacle; terminal and axillary inflorescences positioned above the foliar plane on strong peduncles; inflorescences face mostly upright; freely flowering habit, about 24 inflorescences per plant.

*Fragrance*.—None detected.

*Time to flower*.—Early flowering habit, plants begin flowering about 8.5 weeks after planting; plants flower continuously during the late summer in The Netherlands.

*Post-production longevity*.—Inflorescences maintain good substance for about two to three weeks on the plant; inflorescences not persistent.

*Inflorescence bud*.—Height: About 1.2 cm. Diameter: About 1 cm. Shape: Broadly ovate to globular. Color: Close to 152A; towards the base, close to 144A; towards the apex, close to 72B to 72C.

*Inflorescence size*.—Diameter: About 5.3 cm. Depth (height): About 3.4 cm. Disc diameter: About 5 mm. Receptacle height: About 2 mm. Receptacle diameter: About 7 mm. Receptacle color: Close to 144C.

*Ray florets*.—Quantity per inflorescence: About 80 arranged in about five whorls. Length: About 2.2 cm. Width: About 7 mm. Shape: Obovate, concave. Apex: Broadly acute. Base: Cuneate. Margin: Entire. Aspect: About 20° from horizontal. Texture, upper and lower surfaces: Smooth, glabrous; somewhat velvety. Color: When opening, upper surface: Close to N74C; towards the base, close to 14A to 14B. When opening, lower surface: Close to N74D; towards the margins, close to N74B; towards the base, close to 22A. Fully opened, upper surface: Close to N74D; towards the base, close to 52A tinged with close to 22A; color does not fade with development. Fully opened, lower surface: Close to N74C; towards the base, close to 50A; color becoming closer to N74B with development.

*Disc florets*.—Quantity per inflorescence: About 24. Length: About 8 mm. Diameter: About 1 mm. Shape: Tubular, elongated; apices, acute. Texture, inner and outer surfaces: Smooth, glabrous. Color, when opening and fully opened: Towards the base, close to N25C; towards the apex, close to 46A.

*Phyllaries*.—Quantity per inflorescence: About seven arranged in a single whorl. Length: About 8 mm. Width: About 6 mm. Shape: Obovate. Apex: Obtuse. Base: Broadly cuneate. Margin: Entire. Texture, upper and lower surfaces: Smooth, glabrous. Color, upper and lower surfaces: Close to 137A to 137B.

*Peduncles*.—Length: About 6.6 cm. Diameter: About 2 mm. Aspect: Terminal inflorescences, erect; axillary inflorescences, about 30° from vertical. Strength: Strong. Texture: Smooth, glabrous. Color: Close to 152A tinged with close to N199A.

*Reproductive organs*.—Androecium, present on disc florets only: Quantity per floret: About two. Filament length: About 2 mm. Filament color: Close to 11B. Anther shape: Narrowly oblong. Anther length: About 1.5 mm. Anther color: Close to 13A. Pollen amount: Scarce. Pollen color: Close to 13A. Gynoecium, present on ray and disc florets: Quantity per floret: One. Pistil length: About 7 mm. Style length: About 3 mm. Style color: Close to N25C. Stigma shape: Cleft. Stigma color: Close to 46A. Ovary color: Close to 145B. Seeds and fruits: Seed and fruit development has not been observed on plants of the new *Dahlia*.

Disease/pest resistance: Plants of the new *Dahlia* have not been shown to be resistant to pathogens and pests common to *Dahlia*.

Garden performance: Plants of the new *Dahlia* have been observed to have good garden performance and to tolerate wind and rain. Plants of the new *Dahlia* have been observed to be tolerant to high temperatures of 35° C. and hardy to USDA Hardiness Zone 8.

It is claimed:

1. A new and distinct *Dahlia* plant named 'Bkdapdp' as illustrated and described.

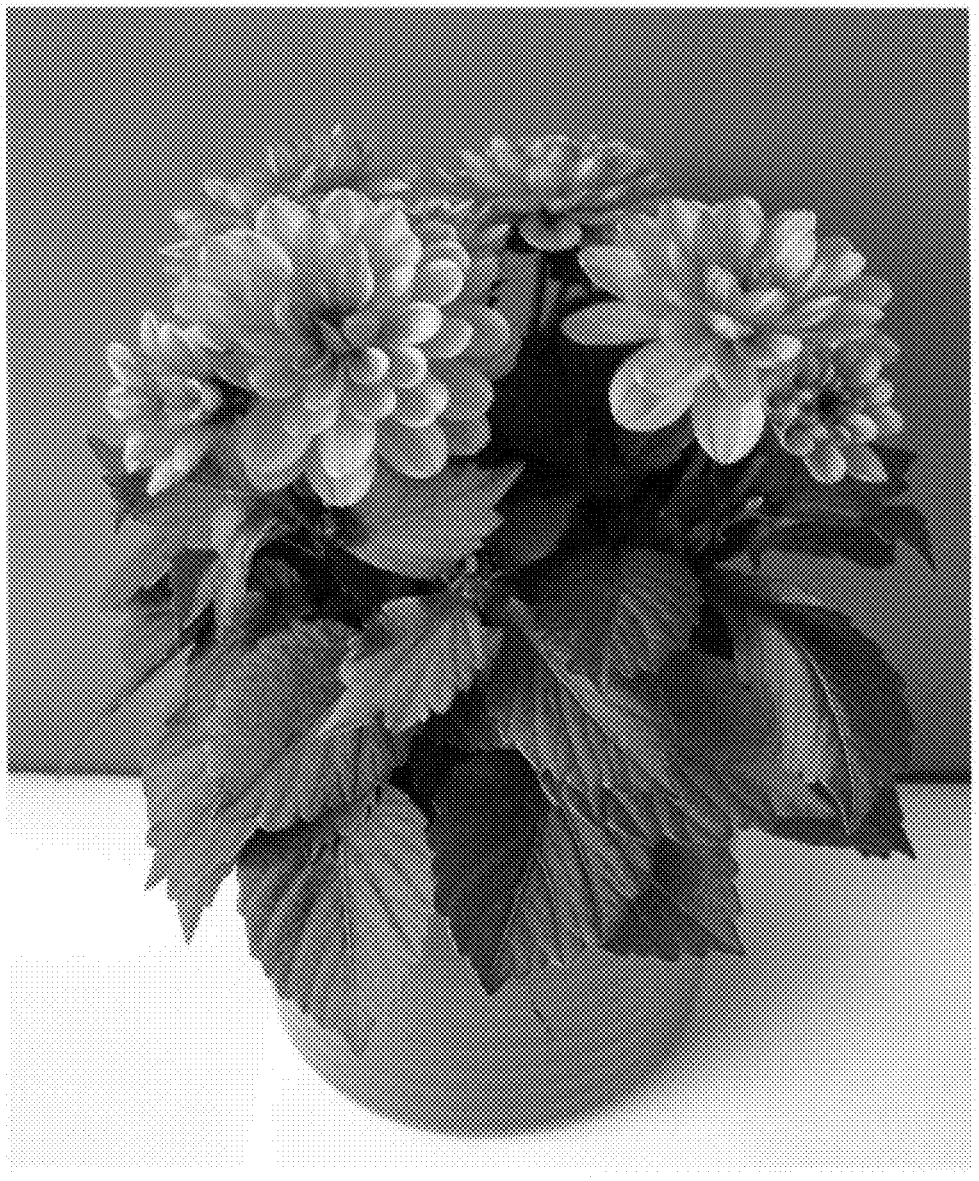

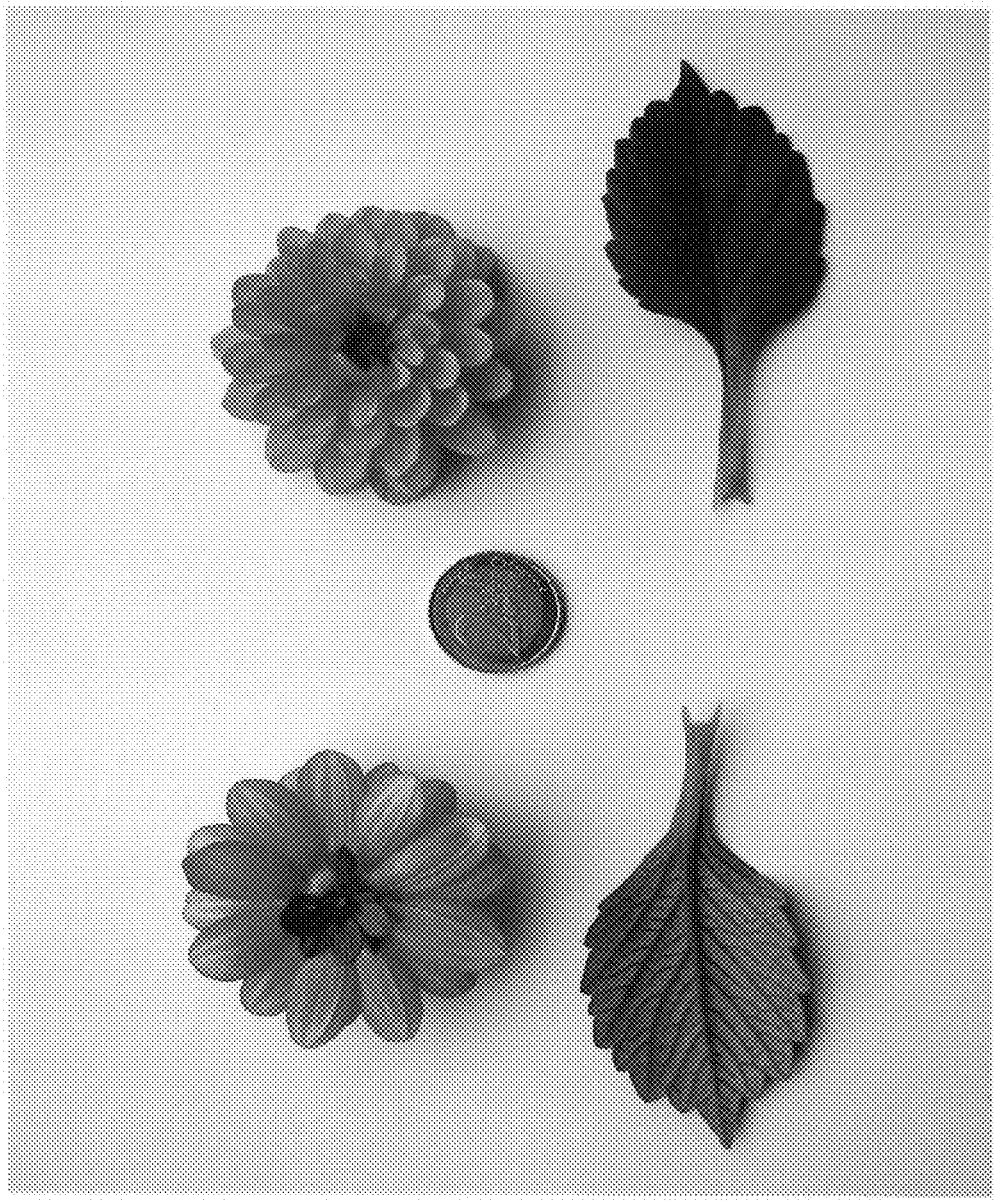

* * * * *